United States Patent
Lan et al.

(10) Patent No.: US 11,576,643 B2
(45) Date of Patent: Feb. 14, 2023

(54) IMAGING PLANNING APPARATUS AND IMAGING PLANNING METHOD

(71) Applicant: CANON MEDICAL SYSTEMS CORPORATION, Otawara (JP)

(72) Inventors: Bing Lan, Chaoyang (CN); Xieping Xu, Chaoyang (CN); Lin Li, Chaoyang (CN); Yijin Wang, Chaoyang (CN); Qingyu Yan, Chaoyang (CN); Naoki Yamashita, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 147 days.

(21) Appl. No.: 16/799,935

(22) Filed: Feb. 25, 2020

(65) Prior Publication Data
US 2020/0268337 A1    Aug. 27, 2020

(30) Foreign Application Priority Data

Feb. 27, 2019    (CN) .......................... 201910144067.5
Dec. 2, 2019    (JP) ............................. JP2019-218085

(51) Int. Cl.
*A61B 6/00*    (2006.01)
*A61B 6/02*    (2006.01)

(52) U.S. Cl.
CPC .............. *A61B 6/542* (2013.01); *A61B 6/027* (2013.01); *A61B 6/463* (2013.01); *A61B 6/5258* (2013.01); *A61B 6/5294* (2013.01)

(58) Field of Classification Search
CPC ......... A61B 6/542; A61B 6/027; A61B 6/463; A61B 6/5258; A61B 6/5294; A61B 6/032
See application file for complete search history.

(56) References Cited

U.S. PATENT DOCUMENTS

| 2012/0230470 A1* | 9/2012 | Bertram .................... G01T 1/02 378/98.5 |
| 2013/0156151 A1 | 6/2013 | Sugaya et al. |
| 2014/0270053 A1 | 9/2014 | Larson |

FOREIGN PATENT DOCUMENTS

| JP | 2012-090887 A | 5/2012 |
| JP | 2012-157468 A | 8/2012 |
| JP | 2014-528284 A | 10/2014 |
| WO | WO 2012/033028 A1 | 3/2012 |

\* cited by examiner

*Primary Examiner* — Courtney D Thomas
(74) *Attorney, Agent, or Firm* — Oblon, McClelland, Maier & Neustadt, L.L.P.

(57) ABSTRACT

An imaging planning apparatus according to one embodiment includes processing circuitry. The processing circuitry obtains a first value of a first index that is related to an X-ray dose and a second value of a second index that is related to an image quality, based on an X-ray imaging condition of a subject set in a predetermined examination. The processing circuitry displays an association chart indicating an association between the first index and the second index on a display unit, displays an acceptable range of the first index and the second index, the acceptable range being based on information related to a diagnostic reference level corresponding to the predetermined examination, in a manner distinguished from a range other than the acceptable range in the association chart, and also displays a mark at a position corresponding to the first value and the second value in the association chart.

19 Claims, 12 Drawing Sheets

IMAGING PLANNING APPARATUS AND IMAGING PLANNING METHOD

CROSS-REFERENCE TO RELATED APPLICATIONS

This application is based upon and claims the benefit of priority from Chinese Patent Application No. 201910144067.5, filed on Feb. 27, 2019; and Japanese Patent Application No. 2019-218085, filed on Dec. 2, 2019, the entire contents of all of which are incorporated herein by reference.

FIELD

Embodiments relates to an imaging planning apparatus and an imaging planning method.

BACKGROUND

In the field of medical device, when an X-ray CT (computed tomography) apparatus or the like scans a subject (patient) using radiation such as X-ray, the scan is usually performed in accordance with a predetermined scan protocol. The so called scan protocol refers to a set of scan parameters used when a scan apparatus such as a CT scanner performs scanning and includes, for example, scan parameters such as the dose of radiation irradiation, the scanning time and the number of uses or the like. In practice, it is very important to select a suitable scan protocol for the CT scan apparatus.

In the prior art, a generally employed method is: a set of scan protocols is pre-set and a plurality of scan protocols are compared utilizing the histogram for selection by the viewer.

In addition, the international standard DRL (Diagnostic Reference Levels) can be used to adjust the scan protocol. DRL is used to identify patient dose levels or the condition of abnormally high dosing activity. If it is found that the DRL is always exceeded when performing a scan protocol or prediction procedure, the procedure and device should be locally checked and the scan protocol should be adjusted to ensure that it has been fully optimized.

A technique of evaluating a scan parameter of a selected scan protocol and generating a signal indicating whether the scan parameters satisfy a scan parameter strategy based on the scan parameters is disclosed in, for example, Patent Document 1 (US 2012/0213326 A1).

However, the existing scan protocol selection methods are not intuitive and it is necessary to check each chart of each scan protocol to obtain detailed information, such that at least three steps are required and the abnormal protocol cannot be intuitively found.

Moreover, the above prior art does not make a suggestion as to how to adjust an abnormal scan protocol and it needs to be performed with the experience of a viewer.

DETAILED DESCRIPTION

Figure 1:
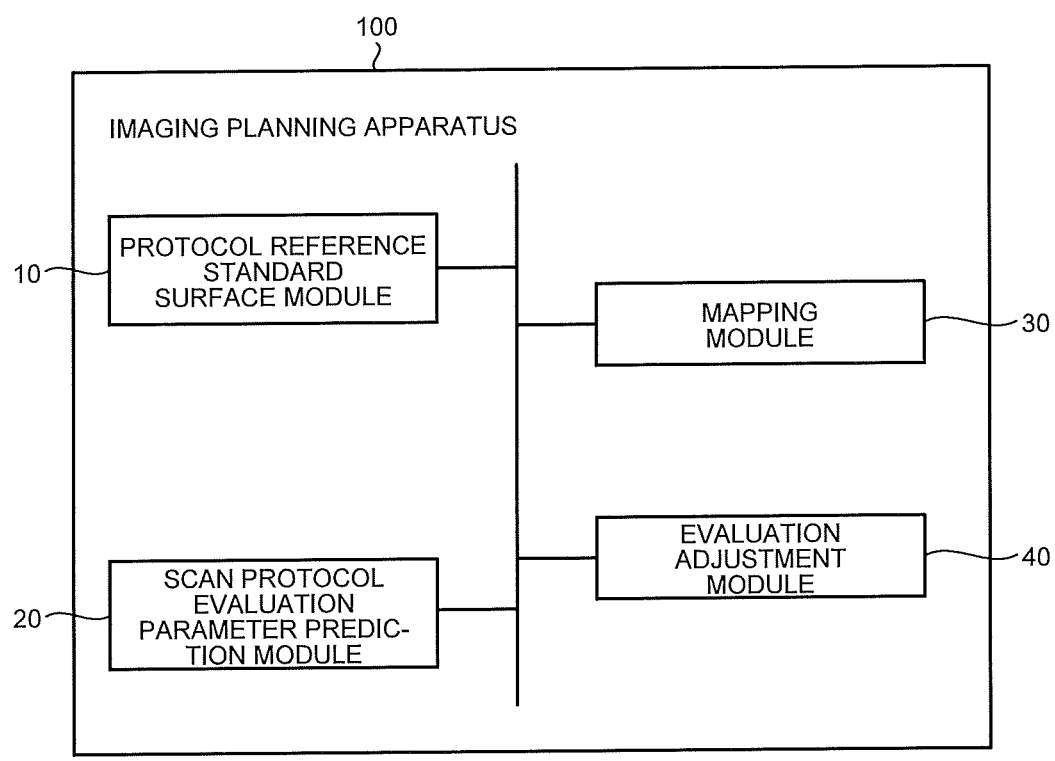
FIG. 1 is a block diagram showing the construction of an imaging planning apparatus in the first embodiment.

An object to be addressed by an embodiment disclosed herein is to provide an imaging planning apparatus and an imaging planning method capable of intuitively displaying an abnormality of the scan protocol. However, without limitation to this object, for example, the achievements of effects derived from various constructions described in Detailed Description of Embodiments below may also be positioned as other objects to be addressed by the embodiments disclosed herein.

The present invention is presented in view of the above issues, aiming to provide a scan protocol adjusting apparatus and a scan protocol adjusting method capable of intuitively displaying the abnormality of the scan protocol and facilitating adjustment of the scan protocol. The scan protocol is also referred to as an imaging plan. Furthermore, the scan protocol adjusting apparatus is also referred to as an imaging planning apparatus. The scan protocol adjusting method is also referred to as an imaging planning method.

An imaging planning apparatus according to one embodiment includes an obtaining unit and a display control unit. The obtaining unit obtains a first value of a first index that is related to an X-ray dose, and a second value of a second index that is related to an image quality, based on an X-ray imaging condition of a subject set in a predetermined examination. The display control unit displays an association chart indicating an association between the first index and the second index on a display unit, displays an acceptable range of the first index and the second index, the acceptable range being based on information related to a diagnostic reference level corresponding to the predetermined examination, in a manner distinguished from a range other than the acceptable range in the association chart, and also displays a mark at a position corresponding to the first value and the second value in the association chart.

One technical solution is a scan protocol adjusting apparatus, comprising: a protocol reference standard surface rendering unit that, based on a specified range of evaluation parameters used when evaluating the scan protocol, calculates and renders a protocol reference standard surface as a reference standard in a space where each evaluation parameter is displayed as a dimension; a scan protocol evaluation parameter prediction unit that predicts the evaluation parameters corresponding to the scan protocol to obtain an evaluation parameter prediction result; a mapping unit that maps the evaluation parameter prediction result to the space; and an evaluation adjustment unit that evaluates or adjusts the scan protocol based on the positional relationship between the evaluation parameter prediction result and the protocol reference standard surface.

Furthermore, it is also possible that the scan protocol adjusting apparatus is located in a scan protocol management server that receives the scan protocol from the medical scan apparatus and broadcasts the adjusted scan protocol to the medical scan apparatus and other medical scan apparatuses. The medical scan apparatus is also referred to as a scan apparatus, a medical image diagnostic apparatus, or a modality, for example. The scan protocol management server is also referred to as a medical information management server.

In addition, it is also possible that the scan protocol adjusting apparatus is located in the medical scan apparatus that receives the scan protocol from the scan protocol management server and converts the scan protocol into a scan protocol suitable for its own type and the scan protocol adjusting apparatus evaluates or adjusts the converted scan protocol using the protocol reference standard surface.

Another technical solution is a scan protocol adjusting method, comprising: a protocol reference standard surface rendering step that, based on a specified range of evaluation parameters used when evaluating the scan protocol, calculates and renders a protocol reference standard surface as a reference standard in the space where each evaluation parameter is displayed as a dimension; a scan protocol evaluation parameter prediction step that predicts an evaluation parameter corresponding to the scan protocol to obtain an evaluation parameter prediction result; a mapping step that maps the evaluation parameter prediction result to the space; and an evaluation adjustment step that evaluates or adjusts the scan protocol based on the positional relationship between the evaluation parameter prediction result and the protocol reference standard surface.

According to the technical solution of the present invention, it is possible to intuitively display an abnormality of the scan protocol and facilitate adjustment of the scan protocol.

The present invention is related to an imaging planning apparatus (also referred to as a "scan protocol adjusting apparatus") and an imaging planning method for adjusting the scan protocol applied when a subject is scanned by a radiation scan apparatus, wherein the scan protocol is a set of scan parameters used when the scan apparatus such as the CT scan apparatus or the like performs scan, and it is possible to select appropriate scan parameters to constitute the scan protocol, according to the type of the scan apparatus and the scanning requirements, the scan protocol for example include at least one of the tube current, the tube voltage, the helical pitch, the scanning range, the scan time, and the slice thickness. The scan protocol is one example of an X-ray imaging condition.

The imaging planning apparatus can be implemented by executing a software having the respective functions of the imaging planning apparatus by a device having a CPU (central processing unit) such as a separate computer disposed in a device such as a scan apparatus or a scan protocol management server. It can also be implemented as a circuit capable of executing various functions of the imaging planning apparatus by means of hardware. Further, the imaging planning apparatus of the present invention may be installed in advance in the above-described scan apparatus as a part of a scan apparatus such as a CT scan apparatus or a magnetic resonance imaging apparatus. In other words, the imaging planning apparatus may be included in a medical image diagnostic apparatus or a medical information management server.

In the following, preferred embodiments of the present invention will be described with reference to the drawings. Moreover, in different embodiments, like reference numbers are used for the same or similar parts and repeated descriptions are appropriately omitted. Furthermore, the embodiments explained below may be combined with one another within the scope in which processes do not contradict with one another.

First Embodiment

FIG. 1 is a block diagram showing the construction of a imaging planning apparatus in the first embodiment. As shown in FIG. 1, the imaging planning apparatus 100 includes a protocol reference standard surface rendering module 10, a scan protocol evaluation parameter prediction module 20, a mapping module 30 and an evaluation adjustment module 40.

Based on a specified range of evaluation parameters used when evaluating the scan protocol, the protocol reference standard surface rendering module 10 calculates and renders a protocol reference standard surface (referred to as PRSS) as a reference standard in a space where each evaluation parameter is displayed as a dimension. The protocol reference standard surface module 10 can be a circuit or software module that is capable of implementing the above functions.

The so called evaluation parameter herein is the evaluation parameter used in evaluating the scan protocol and existing commonly used evaluation parameters may be used. For example, a commonly used evaluation parameter includes a parameter indicating the image quality of the medical image scanned by applying the scan protocol, for example, I image noise, spatial resolution, contrast to noise ratio, low contrast resolution, Z-axis resolution, CNR (contrast-to-noise ratio), SNR (signal-to-noise ratio), etc.; and radiation doses subjected by the subject when the scan protocol is applied, for example, dose index (CTDI: Computed tomography dose index), dose length product (DLP: dose length product), size specific dose evaluation (SSDE), etc. Image quality and radiation dose are regarded more important when evaluating scan protocols. Therefore, image quality and dose are used here as the main evaluation aspects.

It is possible to determine a reasonable range of image quality and dose as a specified range based on different types of scan apparatuses and the characteristics of the subjects. That is, the protocol reference standard surface rendering module 10 takes an acceptable range of threshold values representing image quality and dose as an acceptable range from which the location and size of the protocol reference standard face is determined.

As an example of determining the specified range, the relationship between the evaluation parameters and the diagnostic performance can be obtained based on the study of the historical scanned image and the diagnostic data, in order to determine the acceptable range. In particular, the reasonable range of the evaluation parameters shown by the diagnostic performance model can be determined as the specified range based on the diagnostic performance model representing the relationship between the evaluation parameters and the diagnostic performance. This diagnostic performance model can be externally input directly or can be made based on historical scanned images and diagnostic data. In other words, the protocol reference standard surface rendering module 10 as the display control unit determines the acceptable range based on a diagnostic performance model showing the relationship between the first index (dose) and the diagnostic performance.

Figure 2:
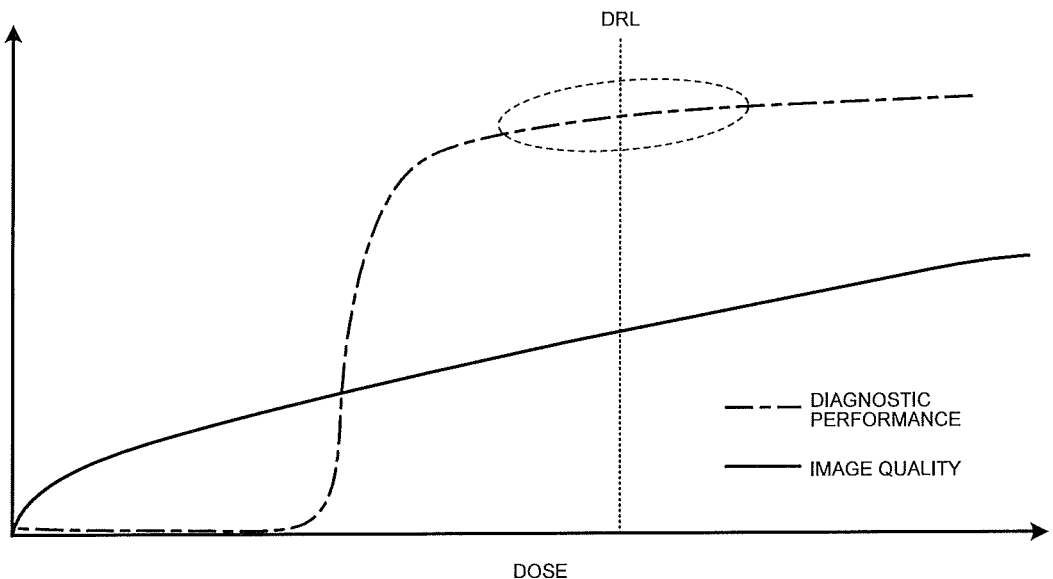
FIG. 2 is a graph showing the relationship between the evaluation parameters and the diagnostic performance.

FIG. 2 is a graph showing the relationship between the evaluation parameters and the diagnostic performance. When the dose is used as the horizontal axis, the trend of diagnostic performance and image quality is shown in FIG. 2. The dose is proportional to the image quality. If the dose is increased, an image with better image quality can be obtained. However, the relationship between the image quality of the medical image and the diagnostic effect (diagnostic performance) obtained when diagnosing with the medical image is not positive proportional relationship. When the image quality is high to a certain extent, even if the image quality is further increased, the diagnostic performance in diagnosis remains at a certain level with little increase. Therefore, an acceptable range can be selected in an interval where the diagnostic performance is already stable. For example, the range of the dose and the image quality corresponding to the diagnostic performance surrounded by the broken line in FIG. 2 can be selected as the specified range. The diagnostic effect indicates how easy a diagnosis is, based on the subjectivity of a person who viewed the medical image (e.g., doctor), for example. The graph shown in FIG. 2 is one example of the diagnostic performance model.

The protocol reference standard surface is a surface showing the acceptable range and is used as a reference standard. Here, the so called acceptable range (specified range) of the evaluation parameter manifests as an entire range of the coordinate values of points in a space constituted by a plurality of evaluation parameters, including the change relation among different evaluation parameters. If two evaluation parameters are selected as dimensions to display a two-dimensional space, the protocol reference standard surface is a surface surrounded by a closed curve composed of a combination (coordinate values) of all evaluation parameters within the acceptable range. In the case where three or more evaluation parameters are selected as dimensions to display a multi-dimensional space, the protocol reference standard surface is a closed surface that encloses a combination of all evaluation parameters within the acceptable range. The closed surface surrounds an closed space, which is preferably a curved surface.

In addition, it is also possible that the protocol reference standard surface rendering module 10 obtains the historical examination data of the evaluation parameters externally, the historical examination data including a combination of the evaluation parameters used to examine the patient in practice, projects a combination of the evaluation parameters into the space, thereby rendering a closed curved surface surrounding all of the points or most points representing the historical examination data in the space as the protocol reference standard surface. For example, the protocol reference standard surface rendering module 10 as the display control unit may obtain a plurality of pieces of past historical examination data that is related to a predetermined examination, and may establish a range where the obtained pieces of historical examination data gather at a concentration of a certain level or higher as the acceptable range.

Figure 4:
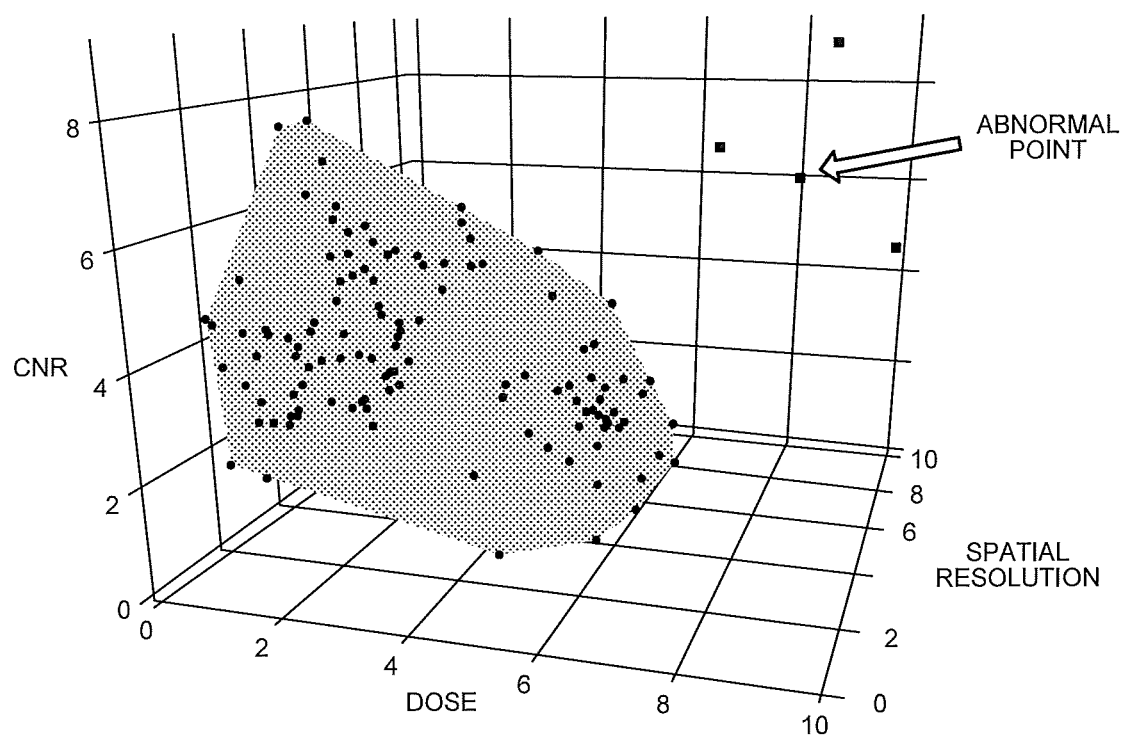
FIG. 4 is a three-dimensional display diagram showing the protocol reference standard surface and the prediction result of an abnormal scan protocol.

FIG. 4 is an example showing the space displayed when the imaging planning apparatus 100 performs the scan protocol adjustment. In the example of FIG. 4, the dose, CNR and spatial resolution are used as dimensions to form a three-dimensional space, wherein the shaded part in FIG. 4 represents the acceptable specified range and the surface surrounding the shaded portion serves as a protocol reference standard surface. The combination of dose, CNR and spatial resolution as evaluation parameters within this acceptable specified range is considered as the scan result for the acceptable scan protocol. The space shown in FIG. 4 is one example of an association chart showing the association between the first index and the second index. The dose is one example of the first index. The spatial resolution and CNR are some examples of the second index. In other words, the association chart represents a space having three or more dimensions including the first index, the spatial resolution, and the contrast-to-noise ratio.

The scan protocol evaluation parameter prediction module 20 predicts an evaluation parameter corresponding to the scan protocol to obtain an evaluation parameter prediction result. The scan protocol evaluation parameter prediction module 20 can be a circuit or software module capable of implementing the above functions.

The scan protocol evaluation parameter prediction module 20 can obtain the prediction result of the evaluation parameter corresponding to the scan protocol by using the existing technology. For example, the scan protocol evaluation parameter prediction module 20 obtains the prediction result by using statistics of the results of the evaluation parameters shown in the history data obtained by applying different scan protocols when scanned previously with the same type of scan apparatus. Alternatively, the scan protocol evaluation parameter prediction module 20 receives the simulation model created for the same type of scan apparatus and substitutes the scan protocol into the simulation model to obtain the prediction result. In addition, all or part of the evaluation parameters may also be data that is input by the operator based on his experience.

The mapping module 30 will map the prediction result of the scan protocol obtained by the scan protocol evaluation parameter prediction module 20 into the space where the protocol reference standard surface is located. The mapping module 30 can be a circuit or software module capable of implementing the above functions.

For example, in the space shown in FIG. 4, a plurality of black dots therein represent the mapping points of the prediction results of respective scan protocols and the position coordinate of each point shows the prediction result. The mapped points correspond one-to-one with the scan protocol to be evaluated. Among them, most of the points fall within the acceptable range surrounded by the protocol reference standard surface and four points do not fall into the closed space surrounded by the protocol reference standard surface.

The evaluation adjustment module 40 evaluates or adjusts the scan protocol based on the positional relationship between the point representing the prediction result and the protocol reference standard surface shown in the space. The evaluation adjustment module 40 can be a circuit or software module capable of implementing the above functions.

Specifically, the evaluation adjustment module 40 determines whether the point representing the prediction result falls within the acceptable range surrounded by the reference standard protocol surface, the scan protocol corresponding to the prediction result that falls within the acceptable range surrounded by the protocol reference standard surface is evaluated as an acceptable scan protocol and the scan protocol corresponding to the prediction result that does not fall within the acceptable range surrounded by the protocol reference standard surface is evaluated as an unacceptable scan protocol and the evaluation result is provided to the scan apparatus.

In addition, it is also possible that the evaluation adjustment module 40 determines whether the point indicating the prediction result falls within an acceptable range surrounded by the protocol reference standard surface and the point that does not fall within the acceptable range surrounded by the protocol reference standard surface is moved into the acceptable range surrounded by the protocol reference standard surface and the scan protocol is adjusted according to the position of the moved point, thereby adjusting the scan protocol to an acceptable scan protocol, and the adjustment results are provided to the scan apparatus. The movement rules of the points can be set arbitrarily.

In addition, various existing methods can be employed by the method of adjusting the scan protocol. For example, the artificial intelligence protocol adjustment model can be used to adjust the scan protocol and the model can be modified by making a feedback.

Figure 3:
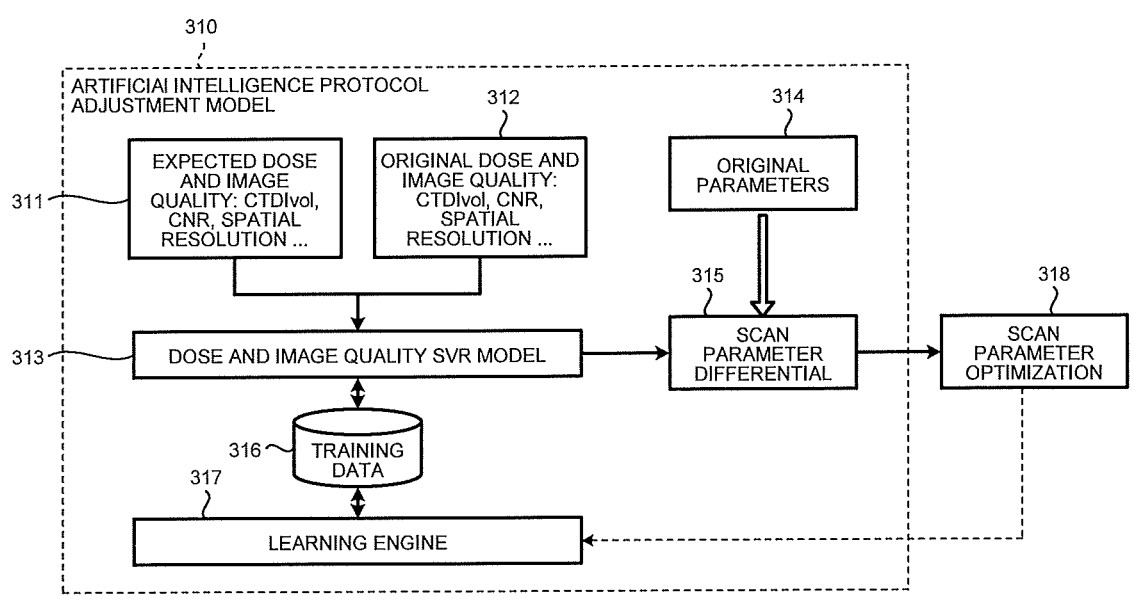
FIG. 3 is a schematic block diagram of an artificial intelligence protocol adjustment model.

FIG. 3 is a schematic block diagram of an artificial intelligence protocol adjustment model. The core model 313 in the artificial intelligence protocol adjustment model 310 is the shown dose and image quality SVR (Support Vector Machine Regression) model. The expected dose and image quality as the adjusted parameters shown in 311: CTDvol, CNR, spatial resolution, etc. and the original dose and image quality at the position of the mapped point as shown in 312: CTDvol, CNR, spatial resolution, etc. are input to the dose and image quality SVR (Support Vector Machine Regression) model, resulting in a differential 315 of the scan parameters in the scan protocol. For example, predicted dose and the image quality 311 are information predicted from the original dose and image quality 312 based on information of a patient who is to be subjected to imaging. The original dose and image quality 312 are historical information of past imaging, or information obtained by simulation. The adjusted optimized scan parameters 318 are obtained by combining the raw scan parameters 314 of the scan protocol prior to adjustment with the differential 315 of the scan parameters.

In addition, the optimized scan parameters 318 can also be fed back to the learning engine 317 for learning and the dose and image quality SVR (Support Vector Machine Regression) model 313 can be refined by using the training data 316. The raw scan parameter 314 is a scan parameter that is pre-set in the medical image diagnostic apparatus, for example.

Figure 5:
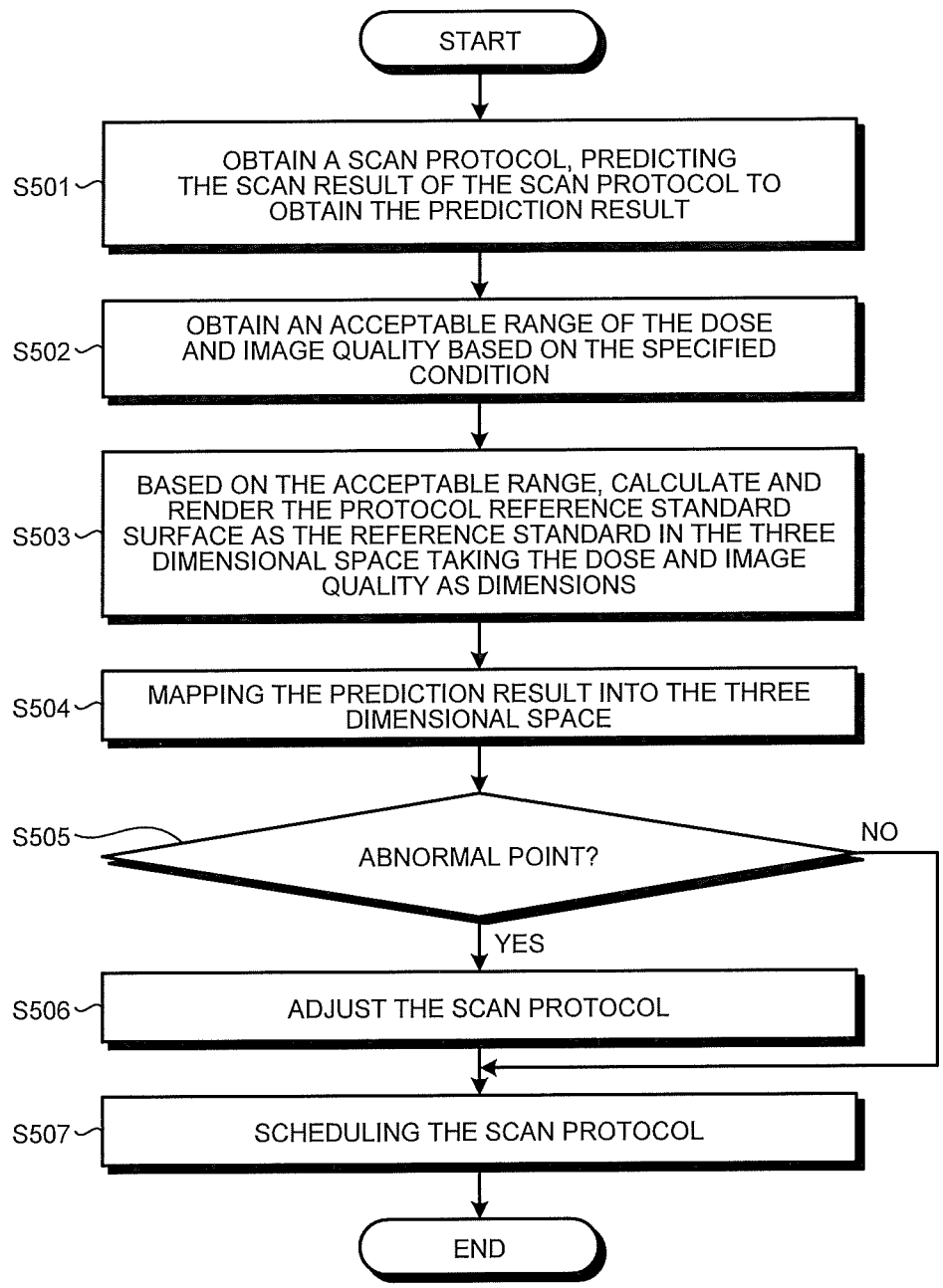
FIG. 5 is a flowchart showing the scan protocol adjustment operations for the imaging planning apparatus in the first embodiment.

In the first embodiment, the protocol reference standard surface rendering module 10 corresponds to "the protocol reference standard surface rendering unit", the scan protocol evaluation parameter prediction module 20 corresponds to a "the scan protocol evaluation parameter prediction unit", the mapping module 30 corresponds to the "mapping unit" and the evaluation adjustment module 40 corresponds to "the evaluation adjustment unit." The flow of the scan protocol adjustment operations in the first embodiment will be illustrated below with reference to FIG. 5.

FIG. 5 is a flowchart showing scan protocol adjustment operations of the imaging planning apparatus in the first embodiment. As shown in FIG. 5, when the adjustment of the scan protocol begins, first, the scan protocol evaluation parameter prediction module 20 obtains a scan protocol, predicts the scan result of the scan protocol to obtain a prediction result as an evaluation parameter corresponding to the scan protocol (Step S501). In other words, the scan protocol evaluation parameter prediction module 20 as the obtaining unit obtains a first value of a first index that is related to an X-ray dose and a second value of a second index that is related to an image quality, based on an X-ray imaging condition of a subject set in a predetermined examination. In the example illustrated in FIG. 4, a value of the dose predicted based on the X-ray imaging condition of the subject corresponds to the "first value", and values of the spatial resolution and the CNR predicted based on the X-ray imaging condition of the subject correspond to the "second value".

Next, the protocol reference standard surface rendering module 10 obtains an acceptable range of dose and image quality according to the conditions specified by the desired image quality, patient information and the like (step S502) and calculates and renders a protocol reference standard surface as a reference standard according to the obtained acceptable range of dose and image quality, for example, uses three parameters in the dose and the image quality as dimensions and displays them in the three-dimensional space as shown in FIG. 4 (step S503). In other words, the protocol reference standard surface rendering module 10 as the display control unit displays an association chart indicating an association between the first index and the second index on a display unit, and displays an acceptable range of the first index and the second index, the acceptable range being based on information related to a diagnostic reference level corresponding to the predetermined examination, in a manner distinguished from the range other than the acceptable range in the association chart.

Next, the mapping module 30 maps the prediction result of the scan protocol obtained by the scan protocol evaluation parameter prediction module 20 in step S501 into the space where the protocol reference standard surface is located (step S504). In other words, the mapping module 30 as the display control unit displays a mark at a position corresponding to the first value and the second value in the association chart.

In step S505, the adjustment evaluation module 40 determines whether the mapped point is an abnormal point based on the positional relationship between the point representing the prediction result mapped by the mapping module 30 and standard protocol reference standard surface. In other words, the evaluation adjustment module 40 as a determining unit determines whether the position corresponding to the first value and the second value in the association chart falls within the acceptable range. If the point representing the prediction result falls within the acceptable range surrounded by the protocol reference standard surface and thus is determined not being an abnormal point (step S505: NO), it proceeds to step S507 and the scan protocol is provided to the scan apparatus, scheduled by the scan apparatus and scan is performed according to the scan protocol.

On the other hand, if the point representing the prediction result as the bold black point in FIG. 4 does not fall within the acceptable range surrounded by the protocol reference standard surface and thus is determined as an abnormal point (step S505: YES), it proceeds to step S506, the evaluation adjustment module 40 adjusts the scan protocol using, for example, the artificial intelligence protocol adjustment model shown in FIG. 3 or the like and the adjusted scan protocol is provided to the scan apparatus, scheduled by the scan apparatus and scan is performed according to the scan protocol (step S507).

In addition, in the flowchart in FIG. 5, the scan protocol evaluation parameter prediction module 20 first obtains the prediction result of the scan protocol and then the protocol reference standard surface rendering module 10 generates the protocol reference standard surface. However, the order of the operations of the scan protocol evaluation parameter prediction module 20 and the protocol reference standard surface rendering module 10 may also be exchanged, that is, step S502 may be performed first and then step S501 may be performed.

In FIG. 5, the mapping module 30 as the display control unit may display the determination result of the determining unit. For example, the mapping module 30 may display information indicating whether the prediction result is at an abnormal point. The information as to whether the prediction result is at an abnormal point may be displayed as text information, or may be displayed graphically, using a color, a shape, or another supplementary mark, or the like of the point indicating the prediction result, for example.

According to the present embodiment, the protocol reference standard surface is used to represent the relationship between the dose and the image quality in the scan result more intuitively, so that the abnormality in scan protocol can be found by intuitively judging the positions of the point and the surface in the created space, thereby the abnormalities in the scan protocol can be displayed intuitively and the adjustment of the scan protocol is facilitated.

Second Embodiment

The second embodiment is based on the first embodiment and differs from the first embodiment in that, in the second embodiment, the imaging planning apparatus 200 further comprising a simulation model establishing module 50 and a guidance information display module 60 and evaluation adjustment module 40 further comprising an acceptance module 41. In the following, description will be made primarily for the difference between the second embodiment and the first embodiment and repeated descriptions are appropriately omitted.

Figure 6:
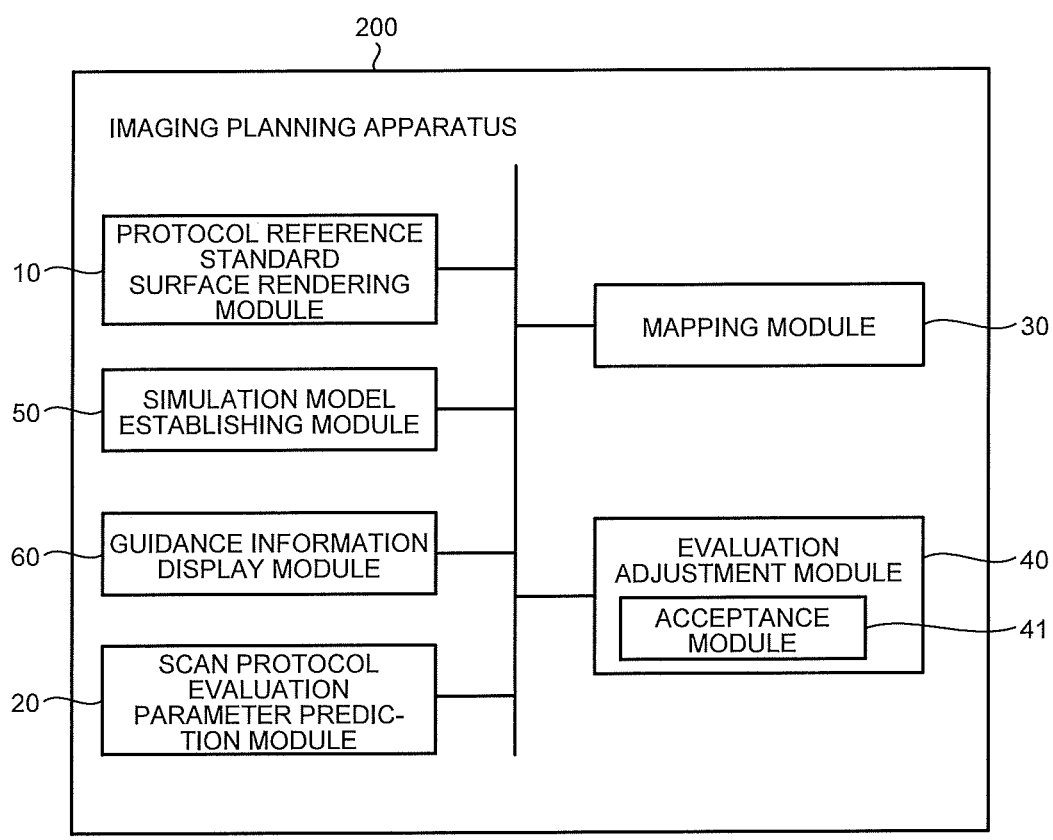
FIG. 6 is a block diagram showing the construction of an imaging planning apparatus in the second embodiment.

FIG. 6 is a block diagram showing the construction of a imaging planning apparatus in the second embodiment. As shown in FIG. 6, the imaging planning apparatus 200 includes a protocol reference standard surface rendering module 10, a scan protocol evaluation parameter prediction module 20, a mapping module 30, an evaluation adjustment module 40, a simulation model establishing module 50 and a guidance information display module 60.

The simulation model establishing module 50 establishes a prediction model for predicting the simulation result based on the historical data of the scan parameters and the patient information. The prediction model establishing module 50 can be a circuit or software module capable of implementing the above functions.

Figure 7:
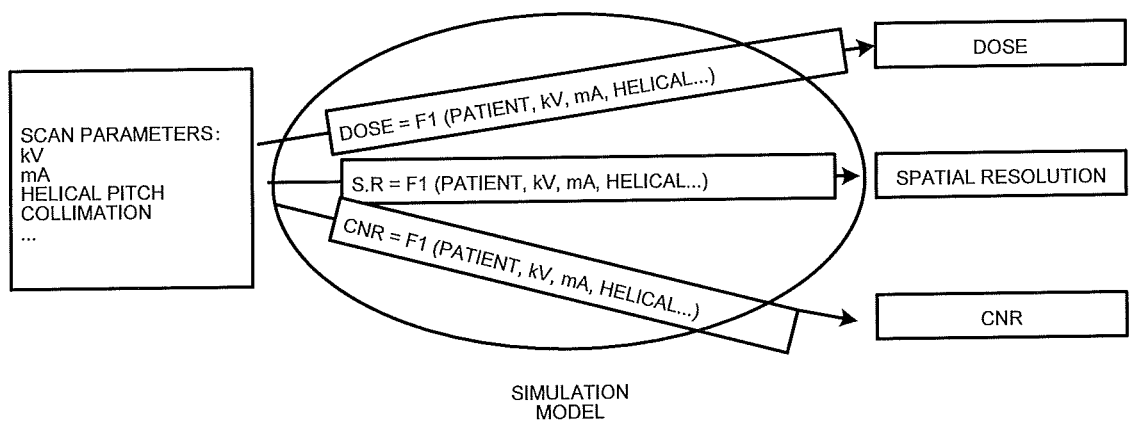
FIG. 7 is a schematic block diagram of a simulation model.

Various existing methods can be applied by the modeling method used by the prediction model establishing module 50. For example, FIG. 7 shows an example of a prediction model. The prediction model shown in FIG. 7 includes equations established by historical data comprising scan parameters such as kV, mA, spiral pitch, collimation and the like as well as patient information. The dose, spatial resolution and CNR values can be obtained when the historical data comprising scan parameters such as kV, mA, spiral pitch, collimation and the like as well as patient information are substituted into the prediction model. In other words, the prediction model establishing module 50 generates a prediction model for predicting the first value of the first index and the second value of the second index, based on the historical data of the scan parameter and the patient information.

The scan protocol evaluation parameter prediction module 20 obtains the evaluation parameters corresponding to the scan protocol as the prediction result with the prediction model established by the prediction model establishing module 50. In other words, the scan protocol evaluation parameter prediction module 20 as the obtaining unit obtains the first value and the second value corresponding to the X-ray imaging condition as a prediction result, using the prediction model.

Further, based on a specified range of evaluation parameters used when evaluating the scan protocol, the protocol reference standard surface rendering module 10 calculates and renders a protocol reference standard surface as a reference standard in the space where each evaluation parameter is displayed as a dimension.

Further, the mapping module 30 maps the prediction result of the scan protocol obtained by the scan protocol evaluation parameter prediction module 20 into the space where the protocol reference standard surface is located.

The guidance information display module 60 can display the guidance information on the display for guiding the operator. In particular, when the mapping module 30 maps the prediction result into said space, the guidance information for guiding the operator's action is displayed. The guidance information can be superimposed and displayed in the space, or it can be displayed separately. The guidance information display module 60 can be a circuit or software module capable of implementing the above functions.

The guidance information may be information that prompts the operator to move the mapping point of the mapping module 30 on the display screen by dragging operation of the mouse, or may be a notice when selecting a scan protocol according to patient information, country, region and the like. For example, when performing a pediatric general chest examination, the following guidance can be displayed.

"Guidance:

For pediatric general chest examinations, children are less interested. Therefore, a larger CNR is needed. We also recommend, on the basis of low tube voltage scan, reducing the radiation dose reduction based on the CNR index.

Recommended appropriate CNR: 12-16 (statistics)

Recommended CTDIvol: 20~30 (ICRP P87 recommends general chest scan)"

In other words, the guidance information display module 60 as the display control unit can display guidance information including at least one of a recommendation mark at a recommended position to which it is recommended that the abnormal point is moved, a path mark indicating a path along which the abnormal point is to be moved to the recommendation mark, and a matter of which an operator is advised to be aware in the predetermined examination.

Moreover, in case the preferred position in the space is used as the recommended movement destination, the guidance information displayed on the display by the guidance information display module 60 may also be information related to the position of the movement destination, thereby the recommended movement destination is prompted to the user, facilitating the user to move the mapped point to the appropriate position. For example, the guidance information may be coordinate information related to the position of the recommended movement destination.

Moreover, the guidance information display module 60 can also directly display the location of the recommended movement destination direct in the display of the space, for example, by using a guide symbol such as an arrow to mark the location of the recommended movement destination in the space, or directly rendering marks such as dots at the position of the recommended movement destination. Thereby, the position of the recommended movement destination of the mapped point is more intuitively shown. For example, the guidance information display module 60 as the display control unit displays a recommendation mark at a recommended position to which it is recommended that the position is moved, when the determining unit determines that the position of the prediction result does not fall within the acceptable range. The recommended position is coordinate information on the association chart, for example. For example, the guidance information display module 60 decides the position (point) nearest to the abnormal point in the acceptable range as the recommended position. The guidance information display module 60 graphically indicates a specific position (recommended position) in the acceptable range, using a color, a shape, or another supplementary mark, or the like, based on the recommended position. As the way in which the recommended position is decided, a wide range of known technologies may be applied, without limitation to the example described above.

The evaluation adjustment module 40 adjusts the scan protocol based on the positional relationship between the point indicating the prediction result and the protocol reference standard surface shown in the space.

In particular, in the second embodiment, the evaluation adjustment module 40 further includes an acceptance module 41 that accepts a movement operation of the prediction result and may be a circuit or software module capable of implementing the above functions.

The operator can move the point mapped in the space by the mapping module 30 to the position desired by himself by dragging operation of the mouse or the like, thereby the acceptance module 41 accepts the position of the moved point. The evaluation adjustment module 40 determines whether the moved point falls within an acceptable range surrounded by the protocol reference standard surface. If the moved point falls within an acceptable range surrounded by the protocol reference standard surface, the scan parameter is derived by using the evaluation parameter corresponding to the position of the moved point, thereby a scan protocol consisting of the calculated scan parameter is provided to the scan apparatus. For example, the evaluation adjustment module 40 as the adjustment unit adjusts the X-ray imaging condition based on a third value of the first index and a fourth value of the second index corresponding to the recommended position. For example, the evaluation adjustment module 40 calculates the X-ray imaging condition corresponding to the coordinate information of the recommended position, via inverse prediction.

Moreover, it is also possible that the operator may directly input the desired scan result using an input device such as a keyboard, and then the acceptance module 41 accepts the operator's input. According to the input data accepted by the acceptance module 41, the position adjustment module 40 moves the corresponding point to the position represented by the data accepted by the acceptance module 41.

If the moved point does not fall within an acceptable range surrounded by the protocol reference standard surface, the evaluation adjustment module 40 determines that the scan protocol corresponding to the moved point is not an acceptable scan protocol. The guidance information display module 60 is further configured to display the guidance information for prompting the operator to perform point position movement, until the moved point falls within an acceptable range surrounded by the protocol reference standard surface.

In the second embodiment, the prediction model establishing module 50 corresponds to the "prediction model establishing unit", the guidance information display module 60 corresponds to the "guidance information display unit" and the acceptance module 41 corresponds to the "acceptance unit". The flow of the scan protocol adjustment operations in the second embodiment will be illustrated below with reference to FIG. 8.

Figure 8:
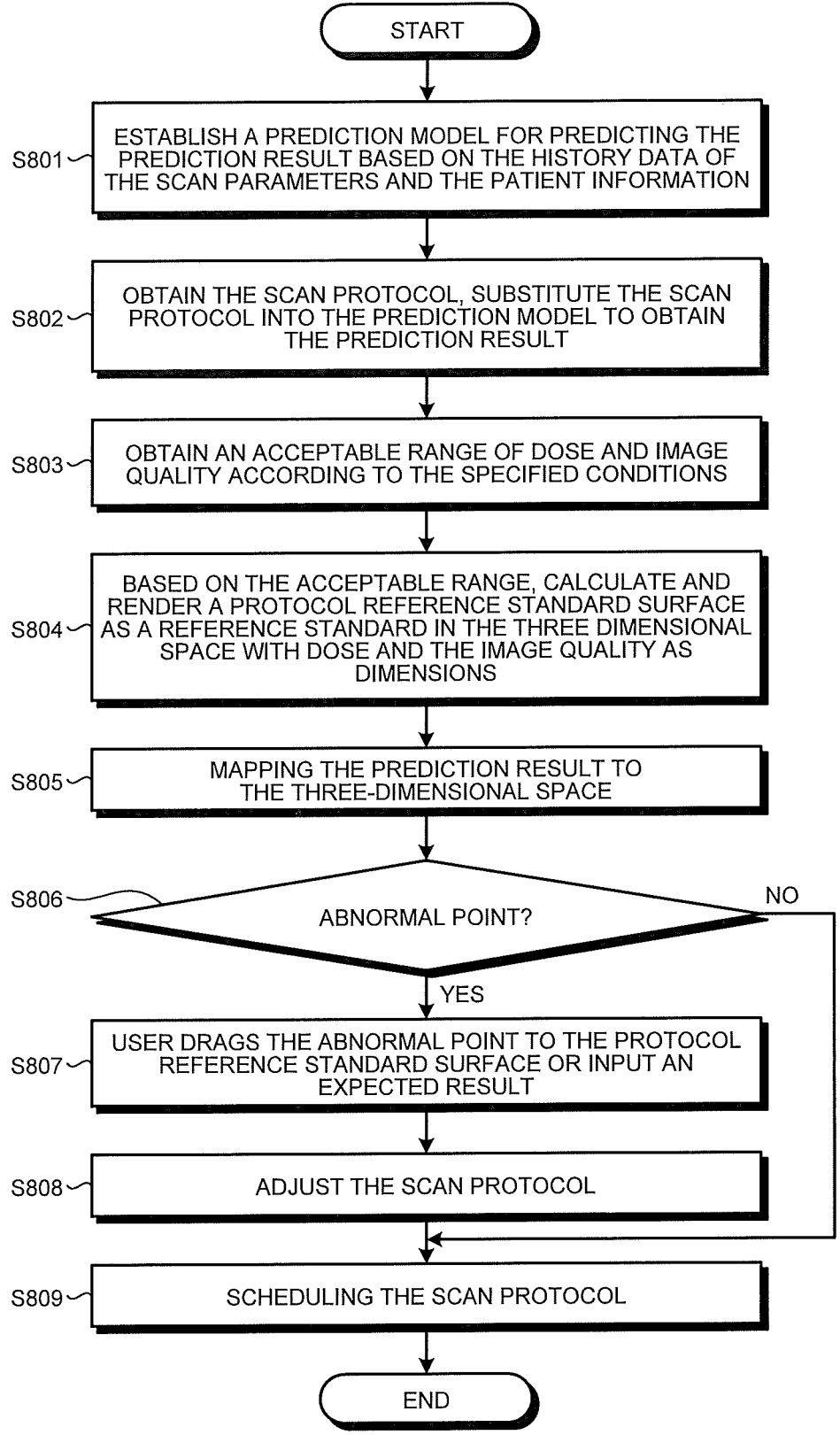
FIG. 8 is a flowchart showing the scan protocol adjustment operations for the imaging planning apparatus in the second embodiment.

FIG. 8 is a flowchart showing scan protocol adjustment operations of the imaging planning apparatus in the second embodiment.

As shown in FIG. 8, when the adjustment of the scan protocol begins, first, the prediction model establishing module 50 establishes a prediction model for predicting the prediction result based on the history data of the scan parameters and the patient information (step S801).

And, the scan protocol evaluation parameter prediction module 20 obtains the scan protocol, substitutes the scan protocol into the prediction model to obtain the prediction result (step S802).

Next, the protocol reference standard surface rendering module 10 obtains an acceptable range of the dose and the image quality according to the conditions specified by the desired image quality, patient information and the like (step S803) and calculates and renders a protocol reference standard surface as a reference standard according to the obtained acceptable range of the dose and the image quality, for example, uses three parameters in the dose and the image quality as dimensions and displays them in the three-dimensional space as shown in FIG. 4 (step S804).

Next, the mapping module 30 maps the prediction result of the scan protocol obtained by the scan protocol evaluation parameter prediction module 20 in step S802 into the space where the protocol reference standard surface is located (step S805).

In step S806, the adjustment evaluation module 40 determines whether the mapped point is an abnormal point based on the positional relationship between the point representing the prediction result mapped by the mapping module 30 and standard protocol reference standard surface. If the point representing the prediction result falls within the acceptable range surrounded by the protocol reference standard surface and thus is determined not being an abnormal point (step S806: No), it proceeds to step S809 and the scan protocol is provided to the scan apparatus, scheduled by the scan apparatus and scan is performed according to the scan protocol.

On the other hand, if the point representing the prediction result as the bold black point in FIG. 4 does not fall within the acceptable range surrounded by the protocol reference standard surface and thus is determined as an abnormal point (step S806: YES), it proceeds to step S807, the operator drags the abnormal point into the closed space surrounded by the protocol reference surface with an input device such as a mouse or the like, or the operator directly inputs the desired scanning result with an input device such as a keyboard or the like. In other words, the acceptance module 41 as the adjustment unit accepts an instruction for moving the mark of the abnormal point displayed on the display unit to a position in the acceptable range, from an operator. For example, the acceptance module 41 accepts the instruction of the operator via a predetermined input interface. The predetermined input interface is an input device such as a mouse and a keyboard.

The evaluation adjustment module 40 adjusts the scan protocol according to the desired scanning result (step S808) and provides the adjusted scan protocol adjustment to the scan apparatus, for scheduling by the scan apparatus for scanning in accordance with the scan protocol (step S809). In other words, the evaluation adjustment module 40 as the adjustment unit adjusts the X-ray imaging condition based on a fifth value of the first index and a sixth value of the second index corresponding to a position specified by the instruction accepted by the acceptance module 41 from the operator.

Moreover, in the flowchart of FIG. 8, the execution order of step S802 and step S803 may be altered.

Moreover, in the present embodiment, the operator is prompted with the guidance information display module 60, so that the operator can perform the determination and adjustment of the abnormal point more efficiently. However, the guidance information display module 60 may be omitted and the operation can be directly conducted by the operator according to his own experience.

According to the present embodiment, an operator may intuitively move the abnormal point to the desired position, with the moving operation, the imaging planning apparatus can output the corresponding adjusted scan protocol directly, so that the scan protocol can be adjusted more conveniently. In addition, it is also possible to visually display an abnormality of the scan protocol and facilitate adjustment of the scan protocol.

Explained above in the second embodiment is an example for displaying the recommendation mark indicating the position of the recommended movement destination, as well as the mark of the abnormal point, but the embodiment is not limited thereto. For example, the imaging planning apparatus may also display the recommendation mark, without displaying the mark at the abnormal point. In other words, in the imaging planning apparatus, the obtaining unit obtains a first value of a first index that is related to an X-ray dose and a second value of a second index that is related to an image quality, based on an X-ray imaging condition of a subject set in a predetermined examination. The display control unit displays an association chart indicating an association between the first index and the second index, and displays an acceptable range of the first index and the second index, the acceptable range being based on information related to a diagnostic reference level corresponding to the predetermined examination, in a manner distinguished from the range other than the acceptable range in the association chart. The determining unit determines whether the position corresponding to the first value and the second value in the association chart falls within the acceptable range. When the determining unit determines that the position of the abnormal point does not fall within the acceptable range, the display control unit displays a mark at a recommended position to which it is recommended that the abnormal point is moved.

Third Embodiment

The imaging planning apparatus of the present invention can be applied to a scan management system composed of a medical scan device and a scan protocol management server. For example, the imaging planning apparatus can be applied to a CT Protocol Management (PM) system. The combination of the imaging planning apparatus and the CT protocol management system will be described below with reference to FIGS. 9 and 10.

Figure 9:
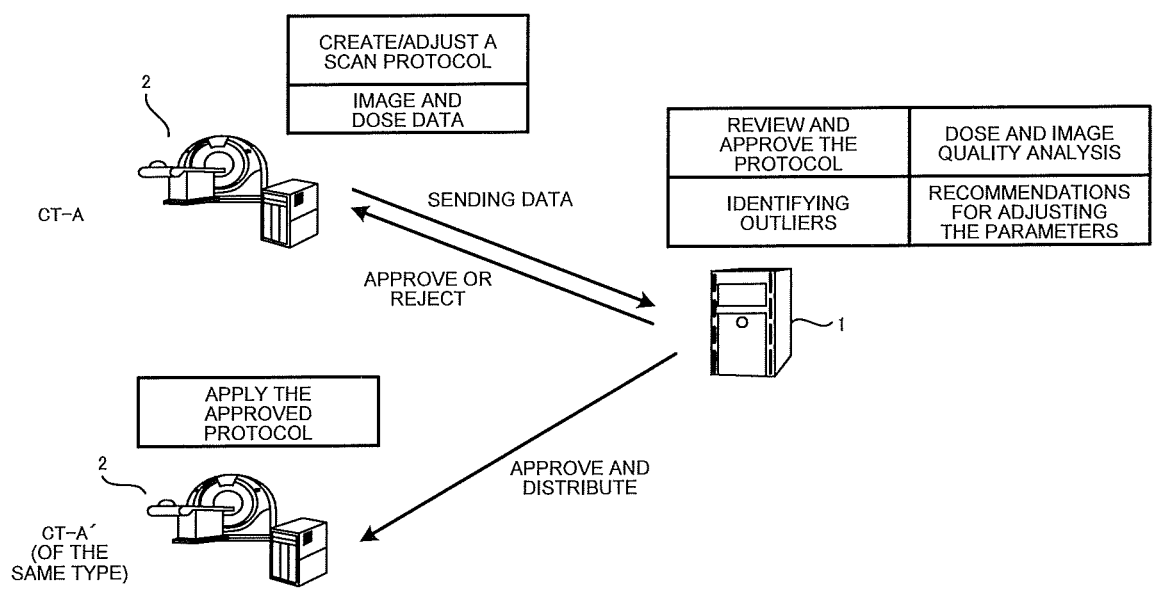
FIG. 9 is a schematic diagram showing the construction of a CT protocol management system in the third embodiment.

FIG. 9 is a schematic diagram showing the construction of a CT protocol management system in the third embodiment. The CT protocol management system includes a scan protocol management server 1 and a plurality of CT scan apparatuses 2 of the same type. Here, for simplification of description, description is made with the example with two CT scanners 2 (CT-A and CT-A'). In the present embodiment, the imaging planning apparatus is installed in the scan protocol management server 1 (medical information management server).

As shown in FIG. 9, the scan protocol management server 1 can make remote communication with the CT scanner 2 wirelessly. Suppose the CT scanner CT-A has created or adjusted a scan protocol and the CT scanner CT-A will send the new protocol to the scan protocol management server 1. On the other hand, the scan protocol management server 1 performs review and approval of the scan protocol. Specifically, the scan protocol management server 1 performs the analysis of the dose and image quality, identifies the abnormal point and adjusts the parameters as described in the first embodiment and the second embodiment above, evaluates or adjusts the scan protocol and broadcasts the adjusted (accepted) scan protocol to the two CT scan apparatuses 2 (CT-A and CT-A'). Thereby, the CT scan apparatus CT-A can perform the scan by applying the adjusted scan protocol. Moreover, the CT scan apparatus CT-A' can also apply the adjusted scan protocol to perform the scan.

Figure 10:
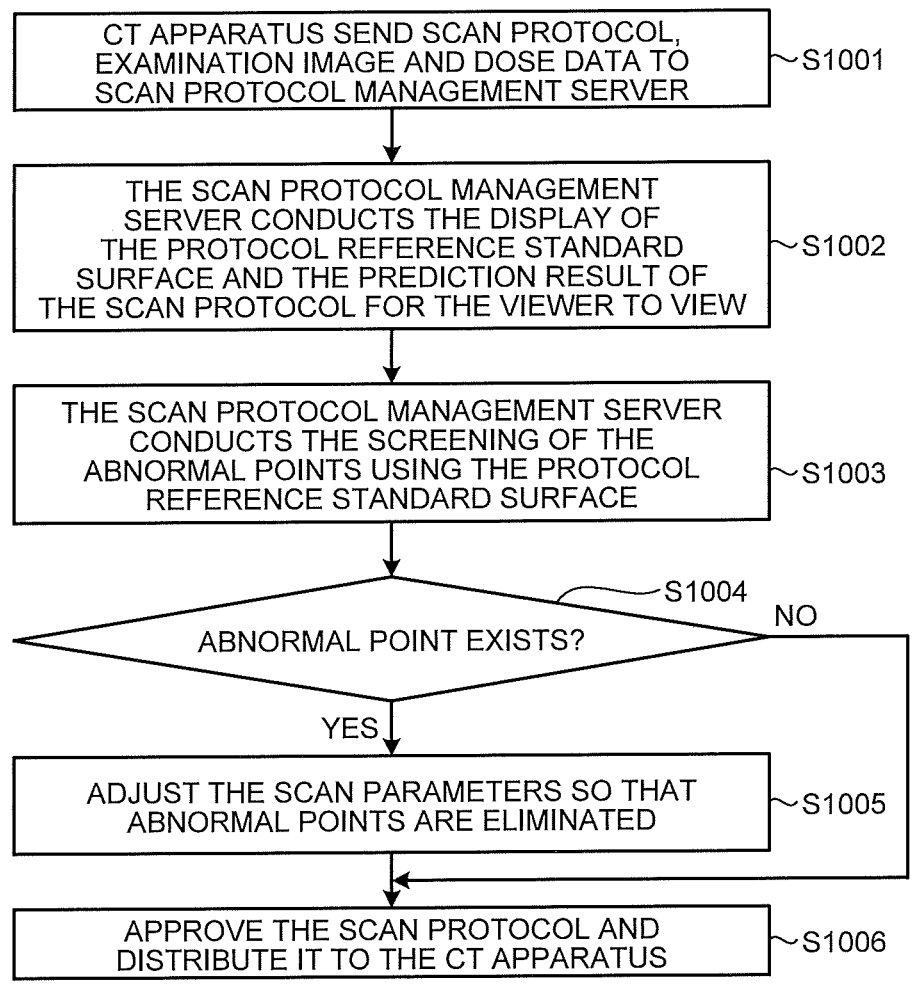
FIG. 10 is a flowchart of a protocol management process of the CT protocol management system in the third embodiment.

FIG. 10 is a flowchart of a protocol management process of the CT protocol management system in the third embodiment. After the CT scan apparatus CT-A has created the scan protocol, it first sends the scan protocol request to the scan protocol management server 1 in order to review the protocol in step S1001. Further, in order to facilitate the scan protocol management server 1 to establish a prediction model or the like, the examination image and the dose data may be sent together.

Next, the scan protocol management server 1 conducts the display of the protocol reference standard surface and the prediction result of the scan protocol for the viewer to view (step S1002) and the scan protocol management server 1 conducts the screening of the abnormal point using the protocol reference standard surface (step S1003). In case it is determined that there is no abnormal point in the space (NO in step S1004), it proceeds to step S1006, the scan protocol management server 1 approves the scan protocol and broadcasts (send) the scan protocol to all CT scan apparatuses.

On the other hand, if it is determined that abnormal points exist in the space (step S1004: YES), it proceeds to step S1005, the scan protocol management server 1 adjusts the scan parameters until no abnormal points exists. Next, the adjusted scan protocol is approved and it is distributed to all CT scan apparatuses (step S1006).

According to the embodiment, remote servers are used for unified control of the scan protocols, scan devices of the same type does not need create a scan protocol and can get the appropriate scan protocol from the scan protocol management server. Thereby the entire CT protocol management system can be improved. Moreover, when the scan protocol management server conducts approval and adjustment of the scan protocols, the abnormalities can be found more intuitively and conveniently, thereby improving the efficiency of the protocol review.

In other words, the scan protocol management server 1 receives an X-ray imaging condition from a medical image diagnostic apparatus, and transmits the X-ray imaging condition adjusted by the adjustment unit to the medical image diagnostic apparatus or another medical image diagnostic apparatus. Explained in the third embodiment is an example in which a medical image diagnostic apparatus (CT-A) and the other medical image diagnostic apparatus (CT-A') are of the same type (model, type), but the embodiment is not limited thereto. For example, when the medical image diagnostic apparatuses are of types that are different from each other, the X-ray imaging condition of one can be converted to that of the other, using a "conversion table" to be described later. The conversion table may be included in the medical image diagnostic apparatus, or in the medical information management server.

Fourth Embodiment

The imaging planning apparatus of the present invention can also be installed to a local scan apparatus for local scan protocol adjustment. Other examples of the combination of the imaging planning apparatus and the CT protocol management system will be described below with reference to FIGS. 11 and 12.

Figure 11:
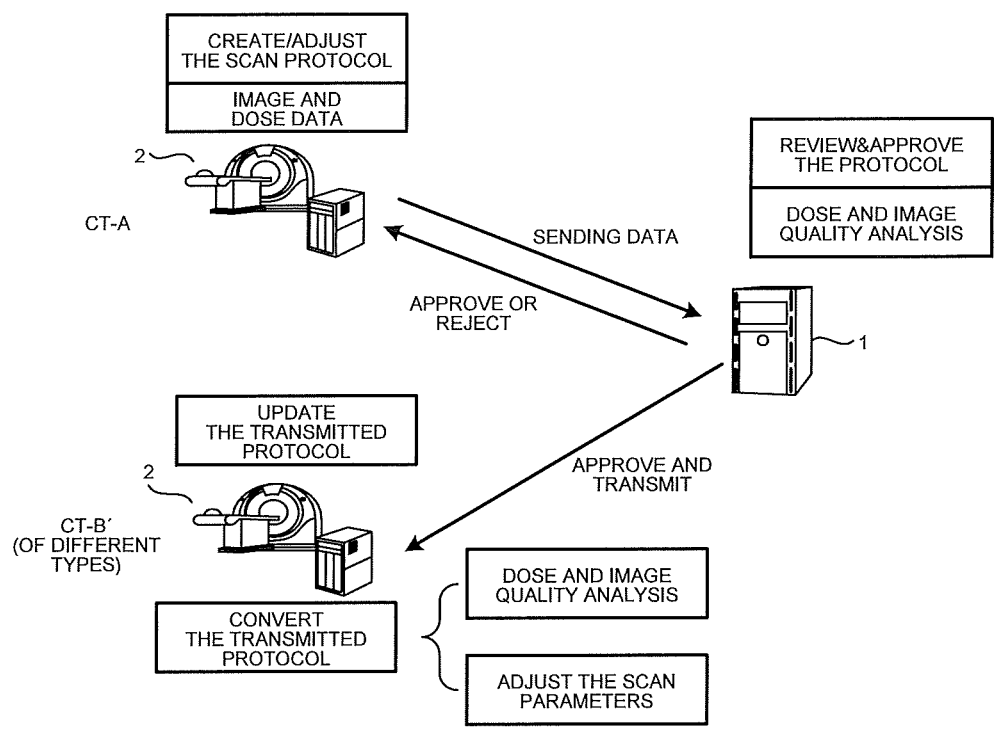
FIG. 11 is a schematic diagram showing the construction of a CT protocol management system in the fourth embodiment.

FIG. 11 is a schematic diagram showing the construction of a CT protocol management system in the fourth embodiment. The CT protocol management system includes a scan protocol management server 1 and a plurality of CT scan apparatuses 2 of different types. Here, for simplification of description, description is made with reference to the example with two CT scanners 2 (CT-A and CT-B'). In the present embodiment, the imaging planning apparatus is installed in the CT scan apparatus CT-B'.

As shown in FIG. 11, the scan protocol management server 1 can make remote communication with the CT scanner 2 wirelessly. Suppose the CT scan apparatus CT-A has created or adjusted scan protocol and the CT scanner CT-A will scan the new protocol to the scan protocol management server 1.

On the other hand, the scan protocol management server 1 performs review and approval of the scan protocol and broadcasts the approved scan protocol to all CT scan apparatuses. The scan protocol management server 1 can employ any method to review the scan protocol.

The CT scanner CT-B' that received the scan protocol converts the received scan protocol to a scan protocol (scan parameters) suitable for its own type and evaluates and adjusts the converted scan protocol. Specifically, the CT scan apparatus CT-B' performs the analysis of the dose and image quality, identifies the abnormal point and adjusts the parameters as described in the first embodiment and the second embodiment above, evaluates or adjusts the scan protocol, thereby apply the adjusted scan protocol.

Figure 12:
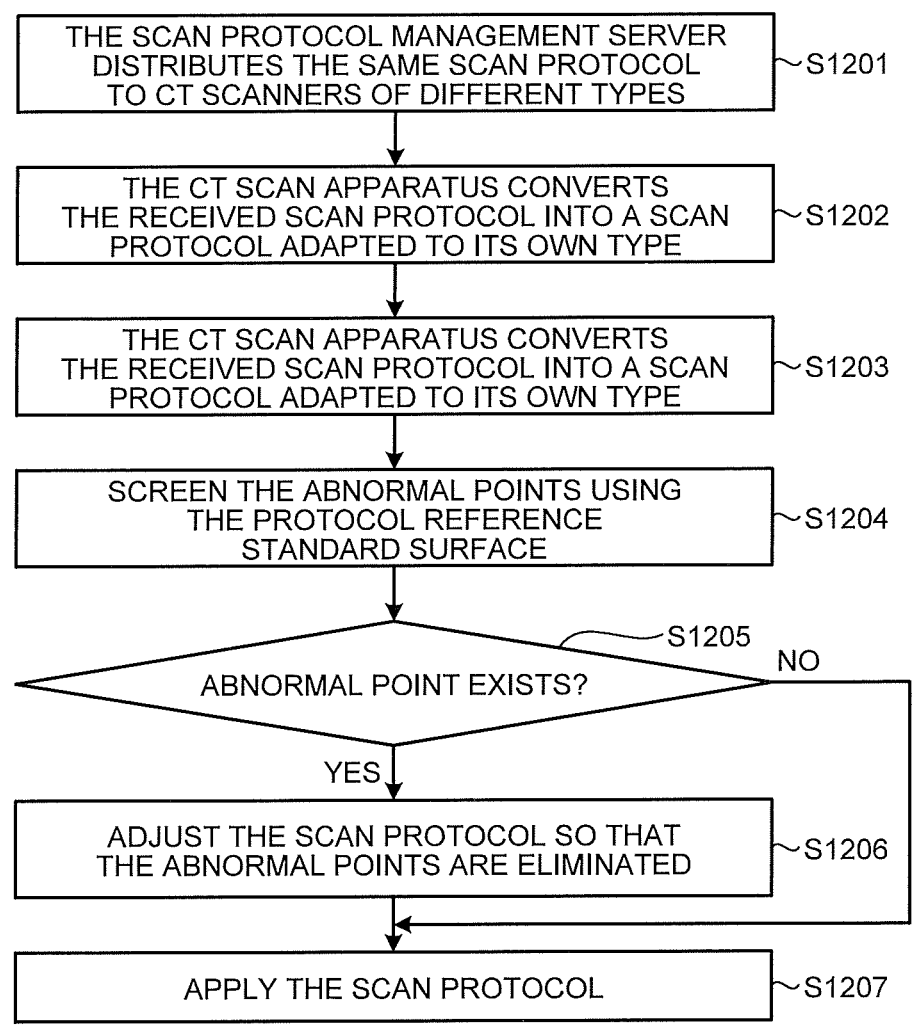
FIG. 12 is a flowchart of a protocol management process of the CT protocol management system in the fourth embodiment.

FIG. 12 is a flowchart of a protocol management process of the CT protocol management system in the fourth embodiment. After the scan protocol management server 1 approves the scan protocol, it first transmits the approved scan protocol to respective CT scanners in step S1201.

Next, the CT scan apparatus CT-B' converts the received scan protocol into a scan protocol adapted to its own model (step S1202) and calculates the predicted result of the image quality and dose using the converted scan parameters (step S1203), thereby screening the abnormal points using the protocol reference standard surface (step S1204). In other words, when the CT scan apparatus CT-B' as the medical image diagnostic apparatus receives an X-ray imaging condition from the medical information management server, the CT scan apparatus CT-B' converts the received X-ray imaging condition to an X-ray imaging condition adapted to its own type. The CT scan apparatus CT-B' then executes various types of processing of the imaging planning apparatus, based on the converted X-ray imaging condition. If it is determined there is no abnormal point in the space (NO in step S1205), it proceeds step S1207 and the CT scan apparatus CT-B' applies the scan protocol.

On the other hand, if it is determined that abnormal points exist in the space (step S1205: YES), it proceeds to step S1206, the CT scan apparatus CT-B' adjusts the scan parameters until no abnormal points exists. Next, the CT scan apparatus CT-B' applies the scan protocol (step S1207).

According to the present embodiment, the local scan apparatus can adjust the convert the scan protocol so that it is more applicable to the scan apparatus itself. Thereby, the management performance of the CT protocol management system mixed with different types of scan apparatuses can be improved. And when conducting adjustment of the scan protocols, the CT scan apparatus CT-B' can find the abnormal more intuitively and conveniently, thereby improving the efficiency of the protocol review.

To convert the scan protocol of one type to that of a different type, a conversion table in which the parameters of one of these scan protocols are associated with those of the other is used. For example, the CT scan apparatus CT-B' includes the conversion table, and converts a scan protocol adapted to the CT scan apparatus CT-A to a scan protocol adapted to its own type, based on the conversion table.

Explained in the fourth embodiment is an example in which each of the CT scan apparatuses has a conversion table, but the embodiment is not limited thereto. For example, the conversion table may be included in the scan protocol management server 1, and not in the CT scan apparatus. In such a case, the scan protocol management server 1 can convert an X-ray imaging condition adjusted by the adjustment unit to an X-ray imaging condition adapted to the type of a receiving medical image diagnostic apparatus, and transmit the converted X-ray imaging condition to the receiving medical image diagnostic apparatus.

In the description of the first embodiment and the second embodiment described above, construction elements of the apparatuses shown in the figures are construction elements of the functional concept and it is not necessarily required to be physically constructed as shown. That is, the specific manner in which the respective apparatuses are distributed or integrated is not limited to the illustration and all or a part thereof may be functionally or physically distributed or integrated in any arbitrary unit in accordance with various loads or usage conditions. Further, with respect to various processing functions performed in various apparatuses, all or any part of it is realized by a CPU (Central Processing Unit) and a program (computer program) analyzed and executed in the CPU, or realized as hardware based on wired logic.

Figure 13:
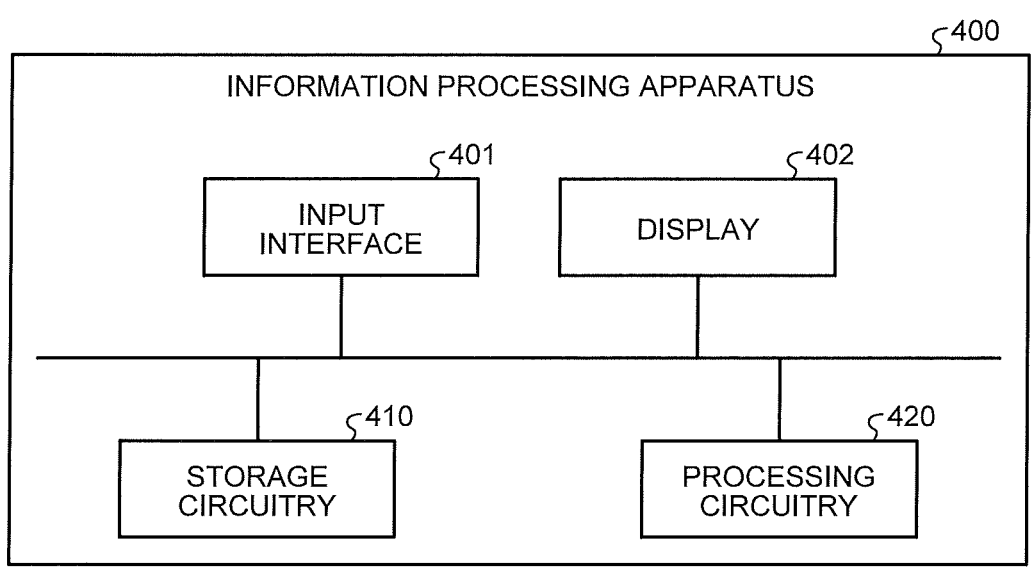
FIG. 13 is a block diagram showing an exemplary construction of an information processing apparatus.

In other words, the imaging planning apparatus 100 illustrated in FIG. 1 is implemented as an information processing apparatus 400 illustrated in FIG. 13. The information processing apparatus 400 corresponds to an apparatus (medical information processing apparatus) capable of processing medical information, such as a personal computer, a workstation, and a console device of a medical image diagnostic apparatus.

FIG. 13 is a block diagram showing an exemplary construction of the information processing apparatus 400. As illustrated in FIG. 13, for example, the information processing apparatus 400 includes an input interface 401, a display 402, a storage circuitry 410, and processing circuitry 420. The input interface 401, the display 402, the storage circuitry 410, and the processing circuitry 420 are communicatively connected to one another.

The input interface 401 includes a mouse, a keyboard, a button, a panel switch, a touch command screen, a foot switch, a track ball, and a joystick, for example, that accept various types of instructions and setting requests from an operator of the information processing apparatus 400. The input interface 401 outputs the accepted various types of instructions and setting requests to the processing circuitry 420.

The display 402 displays, for example, medical image data captured by the medical image diagnostic apparatus, and displays GUI (Graphical User Interface) for enabling a user to enter various setting requests using the input interface 401.

The storage circuitry 410 is implemented as a RAM (Random Access Memory), a semiconductor memory device such as a flash memory, a hard disk, or an optical disc, for example. For example, storage circuitry 410 stores therein the medical image data obtained from the medical image diagnostic apparatus. For example, the storage circuitry 410 stores therein a program for allowing a circuit included in the information processing apparatus 400 to implement its function.

The processing circuitry 420 controls the entire process of the information processing apparatus 400. For example, the processing circuitry 420 includes the protocol reference standard surface rendering module 10, the scan protocol evaluation parameter prediction module 20, the mapping module 30, and the evaluation adjustment module 40 illustrated in FIG. 1. Various processing functions executed by the protocol reference standard surface rendering module 10, the scan protocol evaluation parameter prediction module 20, the mapping module 30, and the evaluation adjustment module 40 are recorded in the storage circuitry 410, as a computer-executable program. The processing circuitry 420 is a processor that reads various programs from the storage circuitry 410, and implements the functions corresponding to the various programs by executing the various programs. To put in other words, the processing circuitry 420 having read the various programs have the various functions illustrated inside the imaging planning apparatus 100 in FIG. 1.

In this embodiment, it is possible to implement various processing functions using the single processing circuitry 420, or to implement the functions by using a combination of a plurality of independent processors as the processing circuitry, and by causing each of the processors to execute a program.

The term "processor" used in the explanation above means a circuit such as a CPU (Central Processing Unit), a GPU (Graphics Processing Unit), an ASIC (Application-Specific Integrated Circuit), a programmable logic device (such as an SPLD (simple programmable logic device), a CPLD (complex programmable logic device), and an FPGA (Field-Programmable Gate Array)). The processor implements a function by reading a program stored in the memory circuit and executing the program. Instead of storing the program in the storage circuitry 410, a program may be incorporated directly into a processor circuit. In such a case, the processor implements the function by reading the program incorporated in the circuit, and by executing the program. The processor according to the embodiment is not limited to an implementation in which each of the processors is configured as one circuit, but it is also possible to use a combination of a plurality of independent circuits as one processor, and to have the one processor to implement the function. It is also possible to integrate the construction elements shown in the figures into one processor, and to have the one processor to implement the function.

The imaging planning apparatus 200 illustrated in FIG. 6 may be implemented as the information processing apparatus 400 illustrated in FIG. 13. In such a case, the processing circuitry 420 includes the protocol reference standard surface rendering module 10, the scan protocol evaluation parameter prediction module 20, the mapping module 30, the evaluation adjustment module 40, the simulation model establishing module 50, and the guidance information display module 60 illustrated in FIG. 6.

Further, in the embodiments above, the imaging planning apparatus may be implemented by a computer like a personal computer or a workstation having a processor and a memory. Now, the program capable of implementing the modules of the imaging planning apparatus is stored in the memory, called by the processor to implement the imaging planning apparatus by the program.

The program can be distributed via a network such as the Internet. In addition, the program can also be recorded on a hard disk, a floppy disk (FD), CD-ROM, MO, DVD and other recording medium that can be read by a computer and read by a computer from the recording medium to be executed.

Several embodiments of the present invention have been described, however, these embodiments are presented as examples and is not intended to limit the scope of the invention. The implementations can be implemented in various other forms and various omissions, substitutions and changes can be made without departing from the spirit of the invention. These embodiments or the variation thereof are included in the scope and spirit of the invention and also included in the invention recited within the claims and equivalents thereof.

What is claimed is:

1. An imaging planning apparatus comprising a processing circuitry configured to:
    obtain a first value of an X-ray dose, a second value of a spatial resolution, and a third value of a contrast-to-noise ratio, based on an X-ray imaging condition of a subject set in a predetermined examination;
    display a graph corresponding to a three-dimensional space with a first dimension representing the X-ray dose, a second dimension representing the spatial resolution, and a third dimension representing the contrast-to-noise ratio on a display;
    display an acceptable range of the X-ray dose, the spatial resolution, and the contrast-to-noise ratio in the graph, the acceptable range being based on information related to a diagnostic reference level corresponding to the predetermined examination, in a manner distinguished from a range other than the acceptable range;
    display a prediction mark in the graph at a position corresponding to the first value, the second value, and the third value;
    determine whether a position of the prediction mark falls within the acceptable range as a determined result; and
    display the determined result.

2. The imaging planning apparatus of claim 1, wherein the X-ray imaging condition includes at least one of a tube current, a tube voltage, a helical pitch, a scanning range, a scan time, and a slice thickness.

3. The imaging planning apparatus of claim 1, wherein, when it is determined that the position of the prediction mark does not fall within the acceptable range, the processing circuitry is further configured to display a recommendation mark at a recommended position to which it is recommended that the position of the prediction mark is moved.

4. The imaging planning apparatus of claim 3, wherein the recommended position is coordinate information on the graph.

5. The imaging planning apparatus of claim 3, wherein the processing circuitry is further configured to graphically indicate a specific position in the acceptable range, based on the recommended position.

6. The imaging planning apparatus of claim 3, wherein the processing circuitry is further configured to adjust the X-ray imaging condition, based on a fourth value of the X-ray dose, a fifth value of the spatial resolution, and a sixth value of the contrast-to-noise ratio corresponding to the recommended position.

7. The imaging planning apparatus of claim 6, wherein
the imaging planning apparatus is included in a medical information management server, and
the medical information management server receives the X-ray imaging condition from a medical image diagnostic apparatus, and transmits the X-ray imaging condition adjusted by the processing circuitry to the medical image diagnostic apparatus or another medical image diagnostic apparatus.

8. The imaging planning apparatus of claim 7, wherein the medical information management server converts the X-ray imaging condition adjusted by the processing circuitry to an X-ray imaging condition adapted to a type of a receiving medical image diagnostic apparatus, and transmits the converted X-ray imaging condition to the receiving medical image diagnostic apparatus.

9. The imaging planning apparatus of claim 1, wherein the processing circuitry is further configured to accept an instruction for moving the position of the prediction mark displayed on the display to a position in the acceptable range from an operator, and adjust the X-ray imaging condition based on a seventh value of the X-ray dose, an eighth value of the spatial resolution, and a ninth value of the contrast-to-noise ratio corresponding to the position included in the instruction.

10. The imaging planning apparatus of claim 9, wherein the processing circuitry is further configured to accept the instruction from the operator via a predetermined input interface.

11. The imaging planning apparatus of claim 1, wherein the processing circuitry is further configured to determine the acceptable range based on a diagnostic performance model indicating a relationship between the X-ray dose, the spatial resolution, and the contrast-to-noise ratio.

12. The imaging planning apparatus of claim 1, wherein the processing circuitry is further configured to obtain a plurality of pieces of past historical examination data related to the predetermined examination, and establish a range where the obtained pieces of historical examination data gather at a concentration of a certain level or higher as the acceptable range.

13. The imaging planning apparatus of claim 1, wherein the processing circuitry is further configured to display guidance information including at least one of a recommendation mark at the recommended position to which it is recommended that the position of the prediction mark is moved, a path mark indicating a path along which the position is moved to the recommendation mark, and a matter of which an operator is advised to be aware in the predetermined examination.

14. The imaging planning apparatus of claim 1, wherein the imaging planning apparatus is included in a medical image diagnostic apparatus or in a medical information management server.

15. The imaging planning apparatus of claim 1, wherein the processing circuitry is further configured to generate a prediction model for predicting the first value, the second value, and the third value based on historical data of a scan parameter and patient information, and obtain the first value, the second value, and the third value corresponding to the X-ray imaging condition using the prediction model, as a prediction result.

16. The imaging planning apparatus of claim 1, wherein
the imaging planning apparatus is included in a medical image diagnostic apparatus, and
when the medical image diagnostic apparatus receives the X-ray imaging condition from a medical information management server, the medical image diagnostic apparatus converts the received X-ray imaging condition to an X-ray imaging condition adapted to its own type, and
the imaging planning apparatus obtains the first value, the second value, and the third value based on the converted X-ray imaging condition.

17. An imaging planning method comprising:
obtaining, via processing circuitry of an image planning apparatus, a first value of an X-ray dose, a second value of a spatial resolution, and a third value of a contrast-to-noise ratio, based on an X-ray imaging condition of a subject set in a predetermined examination;
displaying, via the processing circuitry of the image planning apparatus, a graph corresponding to a three-dimensional space with a first dimension representing the X-ray dose, a second dimension representing the spatial resolution, and a third dimension representing the contrast-to-noise ratio on a display unit;
displaying, via the processing circuitry of the image planning apparatus, an acceptable range of the X-ray dose, the spatial condition, and contrast-to-noise ratio in the graph, the acceptable range being based on information related to a diagnostic reference level corresponding to the predetermined examination, in a manner distinguished from a range other than the acceptable range;
displaying, via the processing circuitry of the image planning apparatus, a prediction mark in the graph at a position corresponding to the first value, the second value, and the third value;
determining, via the processing circuitry of the image planning apparatus, whether a position of the prediction mark falls within the acceptable range as a determined result; and
displaying, via the processing circuitry of the image planning apparatus, the determined result.

18. An imaging planning apparatus comprising a processing circuitry configured to:
obtain a first value of an X-ray dose, a second value of a spatial resolution, and a third value of a contrast-to-noise ratio, based on an X-ray imaging condition of a subject set in a predetermined examination;
display a graph corresponding to a three-dimensional space with a first dimension representing the X-ray dose, a second dimension representing the spatial resolution, and a third dimensions representing the contrast-to-noise ratio;
display an acceptable range of the X-ray dose, the spatial resolution, and the contrast-to-noise ratio in the graph, the acceptable range being based on information related to a diagnostic reference level corresponding to the predetermined examination, in a manner distinguished from a range other than the acceptable range;

determine whether a position corresponding to the first value, the second value, and the third value in the graph falls within the acceptable range; and display, when it is determined that the position does not fall within the acceptable range, a mark at a recommended position to which it is recommended that the position is moved.

19. An imaging planning method comprising:

obtaining, via processing circuitry of an image planning apparatus, a first value of an X-ray dose, a second value of a spatial resolution, and a third value of a contrast-to-noise ratio, based on an X-ray imaging condition of a subject set in a predetermined examination;

displaying, via the processing circuitry of the image planning apparatus, a graph corresponding to a three-dimensional space with a first dimension representing the X-ray dose, a second dimension representing the spatial resolution, and a third dimensions representing the contrast-to-noise ratio;

displaying, via the processing circuitry of the image planning apparatus, an acceptable range of the X-ray dose, the spatial resolution, and the contrast-to-noise ratio in the graph, the acceptable range being based on information related to a diagnostic reference level corresponding to the predetermined examination, in a manner distinguished from a range other than the acceptable range;

determining, via the processing circuitry of the image planning apparatus, whether a position corresponding to the first value, the second value, and the third value in the graph falls within the acceptable range; and displaying, via the processing circuitry of the image planning apparatus and when it is determined that the position does not fall within the acceptable range, a mark at a recommended position to which it is recommended that the position is moved.

\* \* \* \* \*